United States Patent
Seo et al.

(10) Patent No.: US 11,096,671 B2
(45) Date of Patent: Aug. 24, 2021

(54) SPARKLE ARTIFACT DETECTION IN ULTRASOUND COLOR FLOW

(71) Applicant: Siemens Medical Solutions USA, Inc., Malvern, PA (US)

(72) Inventors: Chi Hyung Seo, Sammamish, WA (US); King Yuen Wong, Issaquah, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1685 days.

(21) Appl. No.: 14/850,707

(22) Filed: Sep. 10, 2015

(65) Prior Publication Data

US 2017/0071577 A1    Mar. 16, 2017

(51) Int. Cl.
| | |
|---|---|
| A61B 8/08 | (2006.01) |
| G01S 7/52 | (2006.01) |
| G01S 15/89 | (2006.01) |
| A61B 8/00 | (2006.01) |
| A61B 8/06 | (2006.01) |

(52) U.S. Cl.
CPC .............. *A61B 8/5269* (2013.01); *A61B 8/06* (2013.01); *A61B 8/5207* (2013.01); *G01S 7/5202* (2013.01); *G01S 7/5205* (2013.01); *G01S 7/52026* (2013.01); *G01S 7/52071* (2013.01); *G01S 15/8988* (2013.01); *A61B 8/463* (2013.01); *A61B 8/488* (2013.01); *A61B 8/5223* (2013.01)

(58) Field of Classification Search
None
See application file for complete search history.

(56) References Cited

U.S. PATENT DOCUMENTS

| | | | |
|---|---|---|---|
| 9,318,770 B2 | 4/2016 | Kobayashi | |
| 2007/0078347 A1* | 4/2007 | Srinivasan | G01S 7/5209 600/465 |
| 2008/0021326 A1 | 1/2008 | Bakircioglu et al. | |
| 2009/0253986 A1 | 10/2009 | Frinking et al. | |
| 2010/0185085 A1* | 7/2010 | Hamilton | A61B 8/06 600/437 |

(Continued)

FOREIGN PATENT DOCUMENTS

| | | |
|---|---|---|
| CN | 101897600 A | 12/2010 |
| CN | 103123721 A | 5/2013 |

(Continued)

OTHER PUBLICATIONS

Gao, Jing, et al. "Flow turbulence or twinkling artifact? A primary observation on the intrarenal color Doppler sonography." Clinical imaging 34.5, pp. 355-360, 2010.

(Continued)

*Primary Examiner* — Oommen Jacob
*Assistant Examiner* — Shahdeep Mohammed

(57) ABSTRACT

Sparkle in color flow imaging is detected. Color flow data is estimated with different pulse repetition frequency (PRF). By correlating the color flow data estimated with different PRFs, sparkle is identified. Color flow images may be filtered to reduce motion while maintaining the sparkle region (e.g., kidney stone imaging) or reduce the sparkle region while maintaining motion (e.g., remove sparkle as system noise).

9 Claims, 6 Drawing Sheets

(56) References Cited

U.S. PATENT DOCUMENTS

| | | | |
|---|---|---|---|
| 2011/0164794 A1* | 7/2011 | Zou | A61B 8/06 |
| | | | 382/128 |
| 2011/0263967 A1 | 10/2011 | Bailey et al. | |
| 2012/0046548 A1* | 2/2012 | Hao | A61B 8/14 |
| | | | 600/440 |
| 2013/0336560 A1 | 12/2013 | Wong | |
| 2015/0230777 A1 | 8/2015 | Seo | |
| 2015/0320384 A1* | 11/2015 | Cunitz | A61B 8/0875 |
| | | | 600/424 |

FOREIGN PATENT DOCUMENTS

| | | |
|---|---|---|
| JP | 2000308642 A | 11/2000 |
| JP | 2013-527782 | 3/2015 |

OTHER PUBLICATIONS

Jamzad, Amoon, and Seyed Kamaledin Setarehdan. "Simulation of the twinkling artifact in color flow doppler sonography: a phase noise hypothesis validation." Signal and Image Processing Applications (ICSIPA), Nov. 2011.

Kim, Hyun Cheol, et al. "Color Doppler twinkling artifacts in various conditions during abdominal and pelvic sonography." Journal of Ultrasound in Medicine 29.4, pp. 621-632, 2010.

Tsao, Teng-Fu, et al. "Correlation study of the strength of the color Doppler twinkling artifact with the roughness of the reflecting surface and the Doppler angles." Journal of Medical Ultrasound 12.4, pp. 119-124, 2004.

Office Action dated May 29, 2018 in corresponding Korean Patent Application No. 2016-0116702.

Lan, Yuanpei, et al. "A web-based computer-aided material-selection system for aircraft design." 2010 WASE International Conference on Information Engineering. vol. 3. IEEE, 2010.

Chun, Doo-Man et al: "Web-based material database for material selction and its application programming interface (API) for CAD"; Key Engineering Materials vol. 345-346; pp. 1593-1596; Dec. 31, 2007; Trans Tech Publications; Switzerland.

Sakundarini Novita et al: "Optimal multi-material selection for lightweight design of automotive body assembly incorporating recyclability"; Materials and Design; London, GB; vol. 50; pp. 846-857; XP028552632; ISSN: 0261-3069; DOI: 10.1016/J.MATDES. 2013.03.085.

Cicek K et al: "Multiple attribute decision-making solution to material selection problem based on modified fuzzy axiomatic design-model selection interface algorithm", Materials and Design, London, GB, vol. 31, No. 4, pp. 2129-2133, XP026821195, ISSN: 0261-3069.

Mohammad Hosein Fazel Zarandi et al: "A material selection methodology and expert system for sustainable product design"; The International Journal of Advanced Manufacturing Technology; Springer; Berlin, DE; vol. 57; No. 9-12; pp. 885-903; XP019972388; ISSN: 1433-3015; DOI: 10.I007/S00170-11I-3362-Y.

Hindi, Ammar et al.; "Artifacts in diagnostic ultrasound." In: Reports in Medical Imaging 6, 2013, S. 29-48.

Tanabe, Masayuki et al.; "Effect of pulse repetition frequency on microcalcification detection in color flow imaging." In: Japanese Journal of Applied Physics 53, 07KF15, 2014, pp. 07KF15-1-07KF15-5.

* cited by examiner

SPARKLE ARTIFACT DETECTION IN ULTRASOUND COLOR FLOW

BACKGROUND

This present embodiments relate to sparkle detection in ultrasound color flow imaging. Color flow imaging is susceptible to artifacts when there is a loss of correlation in the backscattered echoes. Correlation loss may be indicative of underlying physiologies, such as kidney stones, due to surface roughness. Correlation loss may instead be due to system imperfections, such as phase noises or reverberation noises. Normally, gain or transmit power is reduced to reduce this sparkle artifact, but at the cost of losing sensitivity. Using spatial variance of the color flow may identify the sparkle, but may reduce aliased flow or turbulence as well as artifacts.

BRIEF SUMMARY

By way of introduction, the preferred embodiments described below include a method, system, computer readable medium, and instructions for sparkle detecting in color flow imaging. Color flow data is estimated with different pulse repetition frequency (PRF). By correlating the color flow data estimated with different PRFs, sparkle is identified. Color flow images may be filtered to reduce motion while maintaining the sparkle region (e.g., kidney stone imaging) or reduce the sparkle region while maintaining motion (e.g., remove sparkle as system noise).

In a first aspect, a method is provided for sparkle artifact detection in color flow. First color flow data representing locations in a patient is generated. The first color flow data is generated with a first pulse repetition frequency. Second color flow data representing the locations in the patient is generated. The second color flow data is generated with a second pulse repetition frequency. A degree of similarity between the first and second color flow data is determined for each of the locations. A color flow image is filtered where the filtering is based on the degree of similarity as a function of location. The filtered color flow image is displayed.

In a second aspect, a non-transitory computer readable storage medium has stored therein data representing instructions executable by a programmed processor for sparkle detection in Doppler imaging. The storage medium includes instructions for: scanning a plurality of locations with ultrasound, the scanning of each of the locations providing a flow sample count of return samples; estimating first Doppler values for the locations using the return samples of the flow sample count; estimating second Doppler values for the locations using a sub-sampling of the return samples of the flow sample count; multiplying the first Doppler values by a factor that is a function of the sub-sampling; correlating the second Doppler values with the multiplied first Doppler values; and detecting the sparkle from results of the correlating.

In a third aspect, a system is provided for sparkle-based processing in flow images. A transducer and beamformer are provided for scanning a scan region. A Doppler estimator is configured to estimate, from the scanning, first motion values representing locations of the scan region and second motion values representing the locations of the scan region. The first motion values are estimated with a different number of samples from the scanning than the second motion values. A processor is configured to identify which of the locations have sparkle from a comparison of the first and second motion values.

The present invention is defined by the following claims, and nothing in this section should be taken as a limitation on those claims. Further aspects and advantages of the invention are discussed below in conjunction with the preferred embodiments.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Sparkling artifacts are detected in ultrasound imaging. Sparkle, sometimes called twinkle, is more random than fluid or tissue motion. Varying pulse repetition frequency (PRF) may produce different information for sparkle artifact. Velocity estimated from blood flow in general is independent of PRF. By generating two images at different PRFs and taking a normalized cross-correlation, a weighting matrix may be applied to produce images with reduced sparkle (e.g., flow only or cleaner flow image) or with reduced flow (e.g., artifact only or enhancing stone). By using PRF variation, sparkle artifacts are detected without affecting sensitivity.

Figure 1:
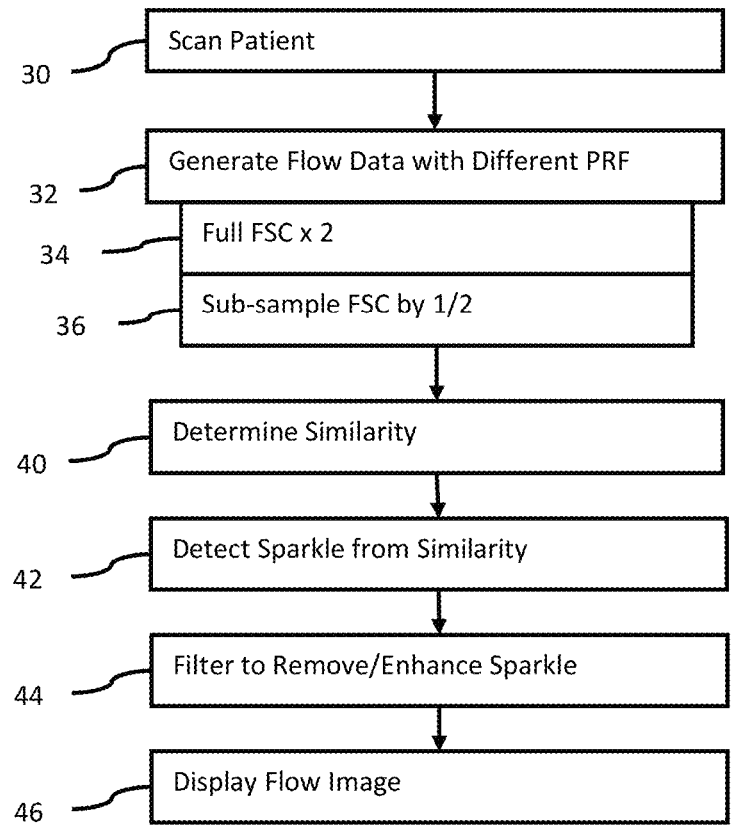
FIG. 1 is a flow chart of one embodiment of a method for sparkle detection in motion imaging.

FIG. 1 shows one embodiment of a method for sparkle artifact detection in color flow. Color flow is used to indicate spatial motion imaging, such as fluid or tissue motion. "Color" is used to distinguish from spectral Doppler imaging, where the power spectrum for a range gate is estimated. The color "flow" data may not be of fluid (e.g., may be of tissue motion) and/or may not represent color (e.g., may be a scalar). The sparkle artifact is detected to enhance return from stones or to reduce system noise for color flow imaging.

Figure 5:
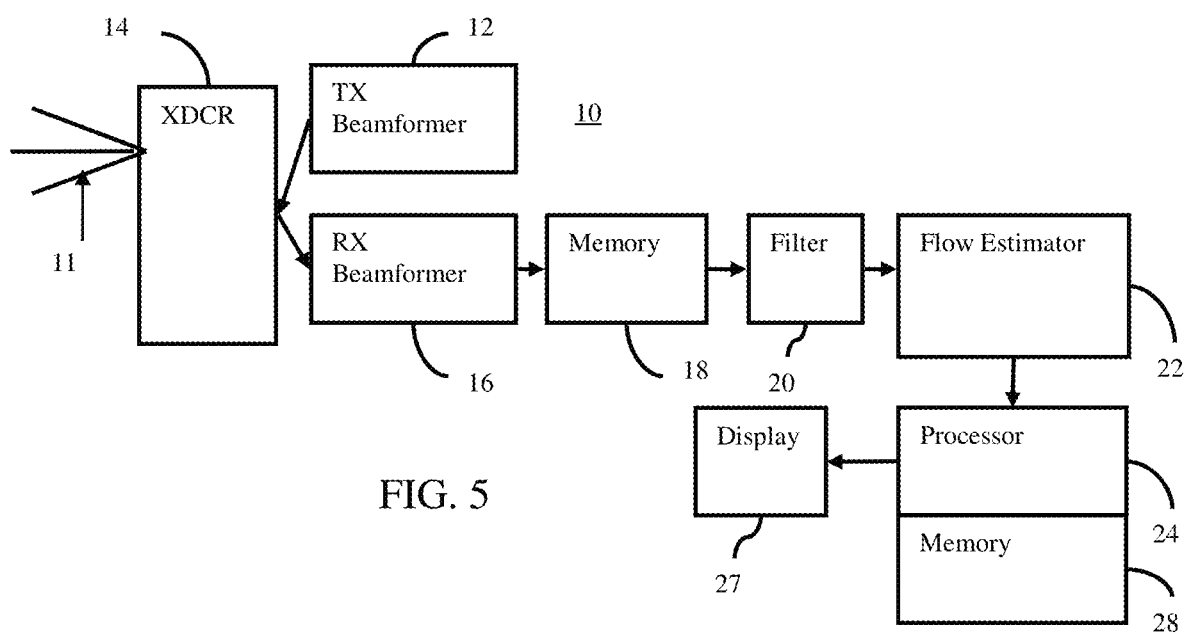
FIG. 5 is a block diagram of one embodiment of a system for sparkle-based processing in flow images.
Figure 2A:
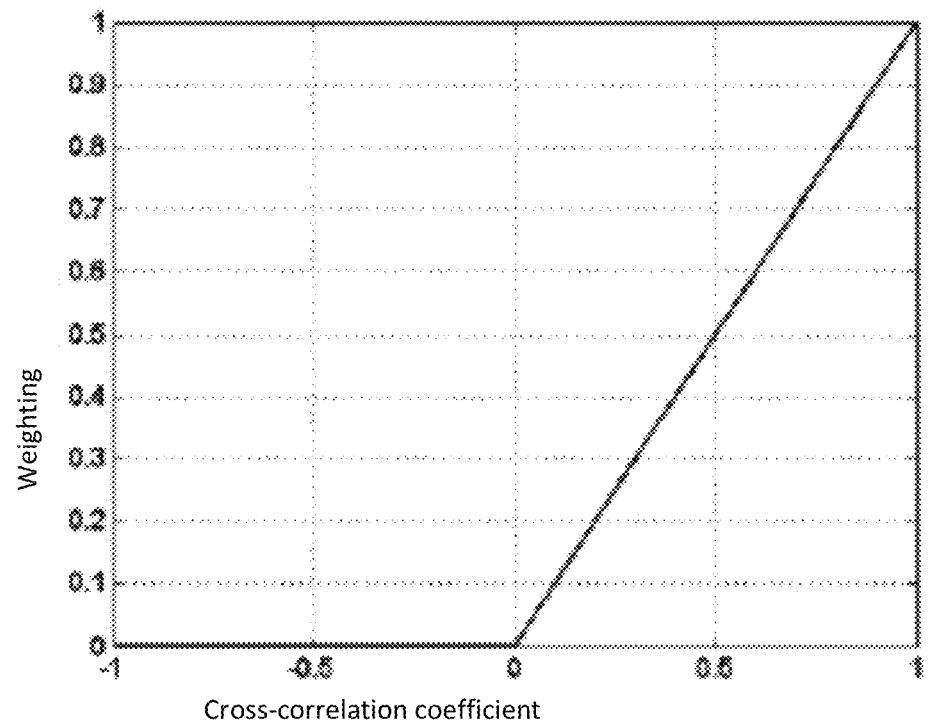
FIGS. 2A-D are example graphs of weights for filtering as a function of the similarity.
Figure 2B:
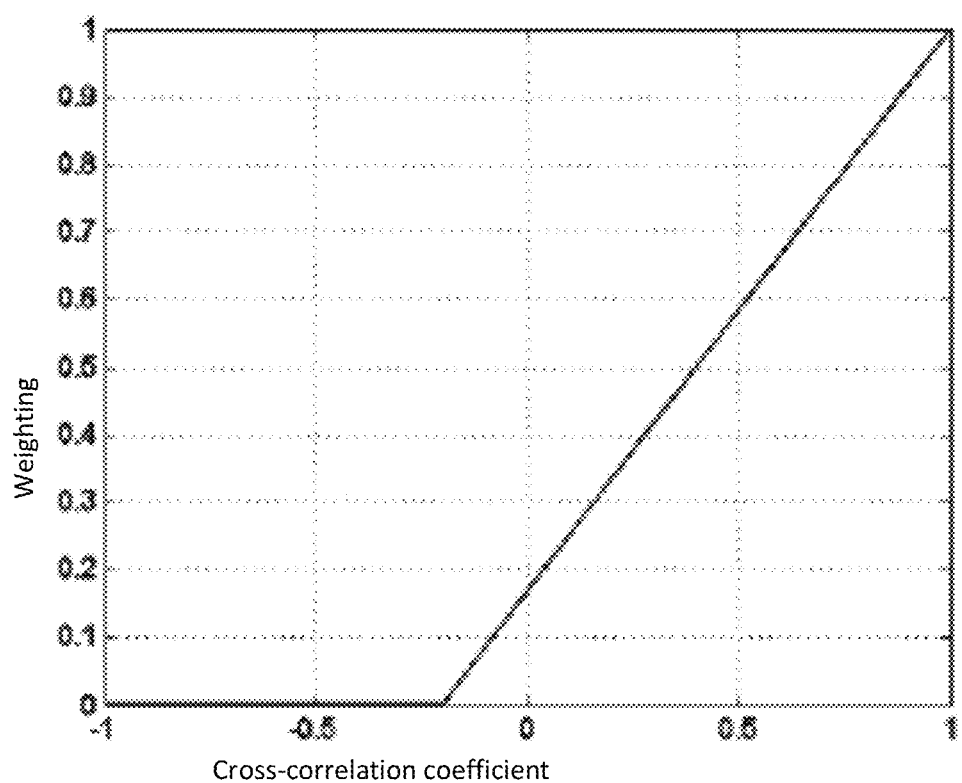
Figure 2C:
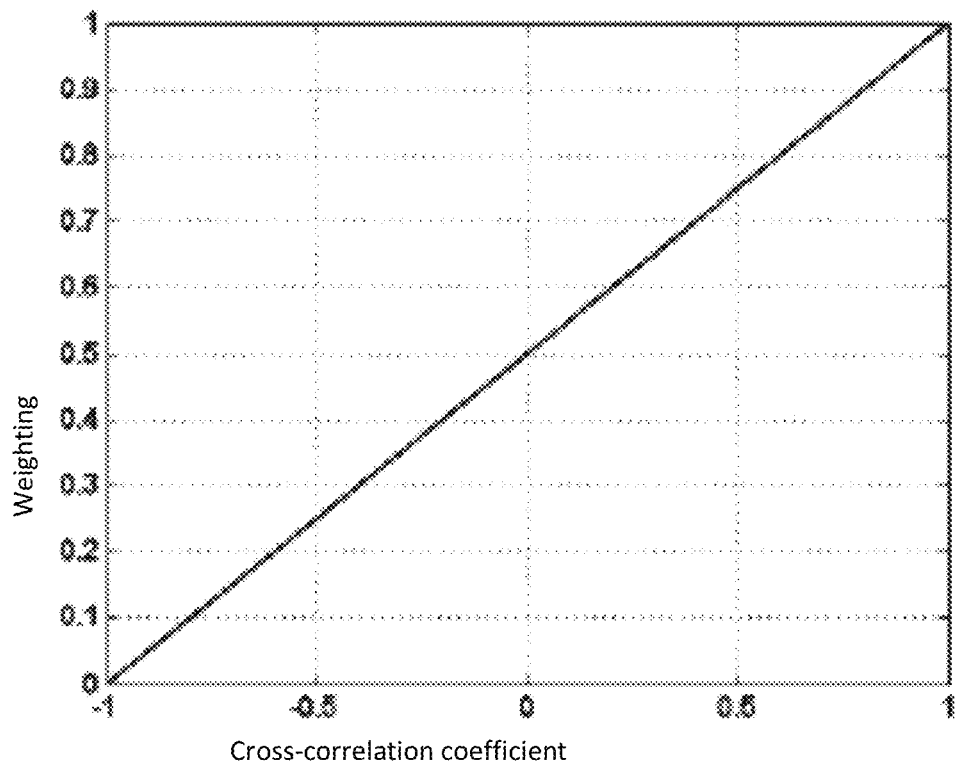
Figure 2D:
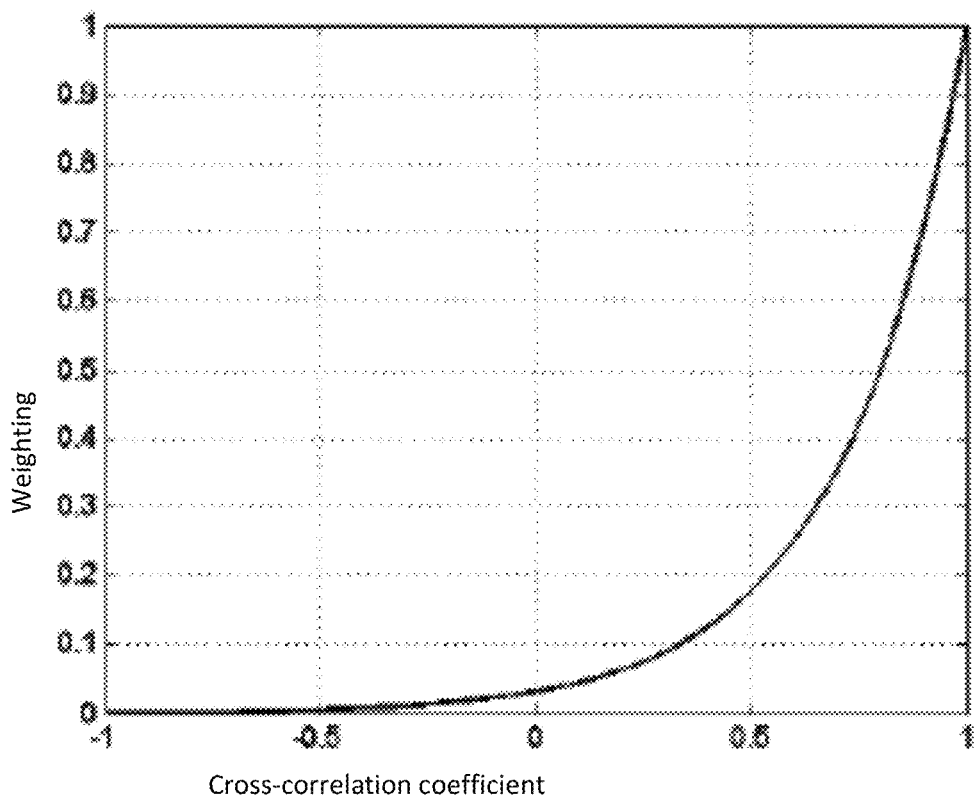

The method is performed by the ultrasound imaging system 10 of FIG. 5, the processor 24, or a different system, filter, and/or processor. For example, the ultrasound imaging system 10 performs the acts. As another example, the processor 24 controls a beamformer for scanning in act 30, causes generation of motion data by a Doppler estimator in acts 32-36, and causes generation of the image by a scan converter, graphics memory, and/or display in act 46, but itself determines similarity in act 40, detects sparkle in act 42, and filters in act 44. In yet another example, a separate filter performs act 44.

The acts of FIG. 1 are performed in the order shown or a different order. For example, acts 34 and 36 are performed in the order shown or an opposite order. As another example, acts 30 and 32 for one PRF are repeated after performing acts 30 and 32 for another PRF.

Additional, different, or fewer acts than shown in FIG. 1 may be used. For example, act 42 is not separately performed, but instead the filtering of act 44 is performed where the similarity indicates the sparkle locations as detection. In another example, an image is not generated in act 46. Acts 34 and 36 are one embodiment for performing act 32, but other embodiments may be provided.

In act 30, various locations within a scan region of the patient are scanned with ultrasound. In one embodiment using an ultrasound system, a patient or region is scanned in real-time with the imaging. The scanned region is an interior of an object, such as the patient. The scan is of a volume, plane, or line region. Scanning a plane provides data representing different locations or samples of the plane. The data representing the region is formed from spatial sampling of the object. The spatial samples are for locations distributed in an acoustic sampling grid.

The region for the color flow scan is a region of interest smaller than a field of view or for the entire field of view. The ultrasound system may scan the field of view using B-mode imaging. The color flow region is a sub-set of that field of view. The user or a processor determines the region of interest in which color flow scanning occurs. Alternatively, the color flow region is the full field of view.

Spatial samples along one or more scan lines are received. Where the transmit beam insonifies just one receive scan line, then return or echo samples along that scan line are received. Where the transmit beam insonifies multiple scan lines, then samples along the multiple scan lines may be received. To generate the samples for different receive beams at a same time, parallel receive beamformation is performed. For example, a system may be capable of forming two or more, tens, or hundreds of receive beams in parallel. Alternatively, signals received from the elements are stored and sequentially processed. Spatial samples are acquired for a plurality of receive lines in the region of interest in response to one and/or in response to sequential transmit beams.

The scanning may be performed a plurality of times to cover the region. The acts are repeated to scan different portions of the region of interest. Alternatively, performing once acquires the data for the entire region of interest.

The complete region of interest is scanned multiple times in sequence. Scanning at different times in sequence acquires spatial samples associated with motion. Any now known or later developed pulse sequences may be used. A sequence of at least two (flow sample count) transmissions is provided along each scan line. For example, the flow sample count is 10-20, resulting in 10-20 samples for each location. Any pulse repetition frequency (i.e., rate of sampling for a location), flow sample count (i.e., number of samples for a location or used to estimate), and pulse repetition interval (i.e., time between each sample acquisition for a location) may be used.

The echo responses to the transmissions of the sequence or return samples are used to estimate velocity, energy (power), and/or variance at a given time. The transmissions along one line(s) may be interleaved with transmissions along another line(s). With or without interleaving, the spatial samples for a given time are acquired using transmissions from different times. The estimates from different scan lines may be acquired sequentially, but rapidly enough to represent a same time from a user perspective. Multiple scans are performed to acquire estimates for different times.

To generate data responsive to different PRFs or flow sample counts, the samples may be acquired with scanning at one PRF or flow sample count. A sub-set of these samples may be used to estimate at the lower PRF. Alternatively, the scanning is repeated. For a first repetition, the return samples are acquired at one PRF. For subsequent repetition, the return samples are acquired at the other PRF. By sequentially transmitting at the different PRFs to acquire return samples in different flow sample counts, samples for estimating flow with different PRF are acquired.

In alternative embodiments, the return samples or estimates of flow are acquired by transfer over a network and/or loading from memory. Data previously acquired by scanning is acquired.

In act 32, an estimator or detector generates color flow data representing locations in the patient. Color flow data includes estimates of velocity, energy (e.g., power), and/or variance. In one embodiment, at least velocity is estimated. The color flow data may be for fluid or tissue. Estimates of velocity, energy, and/or variance of tissue motion may be generated. Any motion data, whether from fluid or tissue movement, may be acquired. Color flow data is used in examples below as motion of fluid, but may alternatively or additionally be tissue motion data.

The received spatial samples may be clutter filtered. The clutter filter passes frequencies associated with fluid and not tissue motion or with tissue motion and not fluid. The clutter filtering is of signals in the pulse sequence for estimating motion at a given time (e.g., samples of the flow sample count). A given signal may be used for estimates representing different times, such as associated with a moving window for clutter filtering and estimation. Different filter outputs are used to estimate motion for a location at different times.

Color flow data is generated from the spatial samples. Doppler processing, such as autocorrelation, may be used. In other embodiments, temporal correlation may be used. Another process may be used to estimate the color flow data. Color Doppler parameter values (e.g., velocity, energy, or variance values) are estimated from the spatial samples acquired at different times. The change in frequency (e.g., Doppler shift) between two samples for the same location at different times indicates the velocity. A sequence (flow sample count) of two or more samples may be used to estimate the color Doppler parameter values. Estimates are formed for different groupings of received signals, such as completely separate or independent groupings or overlapping groupings. The estimates for each grouping represent the spatial location at a given time.

The estimation is performed for the different sampled spatial locations. For example, velocities for the different locations in a plane are estimated from echoes responsive to the scanning. Multiple frames of color flow data may be acquired to represent the region of interest at different times, respectively.

The estimates may be thresholded. Thresholds are applied to the velocities and/or powers. For example, a low velocity threshold is applied. Velocities below the threshold are removed or set to another value, such as zero. As another example, where the energy is below a threshold, the velocity value for the same spatial location is removed or set to another value, such as zero. Alternatively, the estimated velocities are used without thresholding.

The acquired motion or color flow data is a frame of data or image representing the patient at a given time, despite being estimated from received signals over the flow sample count. Other data may be generated, such as B-mode data.

A B-mode image may be overlaid with or have an incorporated region of interest showing the color Doppler velocities. Within the region of interest, locations with no flow are shown as B-mode data.

To detect sparkle, two or more frames of data representing the same locations but at different PRF are generated. By generating the frames from the same data, the locations are the same. Where the frames are generated with sequential scanning, the same locations may not be exactly the same due to transducer and/or tissue motion, but are generally the same.

Acts 34 and 36 show one embodiment where the two frames with different PRF are generated using a factor of 2. In act 34, one frame of data is generated for one PRF. For example, Doppler values are estimated using the return samples of one flow sample count (e.g., 16). Velocities or other motion values are estimated for each of the locations using the PRF and corresponding flow sample count.

The true velocity $v_t$ of a flow pixel may be expressed as:

$$v_t = \arg \sum_i z(i) \times z^*(i-1) = 2n\pi + v_d$$

where z is the color ensemble samples, $v_d$ is the Doppler velocity estimate, i is an index of the samples, n is an integer, and $-\pi \leq v_d < \pi$. The velocity image or frame of velocity values may be expressed as $$vel_{image} = v_t \mod 2\pi = v_d$$

Other expressions of the frame of velocity values may be used.

Where the values are to be estimated from the same flow sample count, the PRF for one of the frames is the full or all of the flow samples, providing the maximum PRF given the acquired samples. Alternatively, sub-sampling is used (e.g., acquire 20 samples for the flow sample count, but use just 16).

For the frame of data with the greater PRF, the estimated velocities are multiplied by a factor. The factor is related to or the same as the amount of sub-sampling for the other PRF or is a reflection of the difference in PRFs. For example, sub-sampling the flow sample count by a factor of 2 doubles the resulting velocity values. For more exact comparison, the estimates of velocity using the full or greater flow sample count (i.e., twice the PRF) are multiplied by 2. $\{2v_d\}$ mod $2\pi$ is simply the original image multiplied by 2 and then wrapped by $2\pi$.

Any multiplication may be used, such as multiplying the estimated velocities by the factor. In one embodiment, the velocities are multiplied by 2 using finite precision arithmetic so that the wrapping is inherent during overflow (i.e., if the original velocities are 8-bit 2s complement, performing the multiply by 2 in 2s complement arithmetic automatically achieves the desired multiplication). Where the factor is other than two, the multiplication may be expressed as:

$$vel_{times\delta} = \{\delta v_d\} \mod 2\pi$$

Alternatively, the estimated velocities are not multiplied by the factor. The correlation for detecting sparkle relies on variation by location, so having similar magnitudes for each location may not be needed in some cases of no wrapping.

For comparison to the motion data with one PRF, motion data is generated with another PRF in act 36. The Doppler estimator generates a second frame of color flow data representing the locations in the patient. The second frame of color flow data is generated with a second pulse repetition frequency. A different flow sample count is used. The same set of return samples or a different set of return samples are used. For estimating Doppler values from a different set, the different set has a different flow sample count and/or PRF. For estimating Doppler values from a same set, sub-sampling is used. The same return samples are sub-sampled to decrease the PRF and reduce the flow sample count.

Any reduction or sub-sampling may be used. For example, the flow sample count is reduced by half or a factor of 2. Every other (e.g., samples 1-16 used for one frame and only even or odd number samples used for the other frame) or other grouping results in use of half of the return samples. Every third, or other grouping using fewer than all, fewer than half, and/or fewer than used for the other frame of velocity values may be used. Any integer or real value sub-sampling factor may be used.

In one representation, a subsampled image $vel_{subsampled}$ is created as:

$$vel_{subsampled} = \left\{\arg \sum_i z(2i) \times z^*(2i-2)\right\} \mod 2\pi$$

For true blood flow, the subsampled image using a factor of 2 is expected to be twice the true velocity, as represented as:

$$\arg \sum_i z(2i) \times z^*(2i-2) \approx 2v_t$$

Applying this approximation to the subsampled image gives:

$$vel_{subsampled} \approx \{2v_t\} \mod 2\pi = \{4n\pi + 2v_d\} \mod 2\pi = \{2v_d\} \mod 2\pi,$$

indicating that the velocity has a magnitude greater than the true velocity by the sub-sampling factor. The velocities estimated with twice the PRF results in velocities having twice the magnitude of velocities estimated with the PRF.

Since sub-sampling by other factors than 2 may be used, more than one frame of sub-sampled velocity data may be generated. For example, motion data are generated with sub-sampling factors of 2 and 3. The resulting frames may be averaged or otherwise combined. Multiple versions of $vel_{subsampled}$ are averaged to increase accuracy of true velocity before performing correlation. For example, arg $\Sigma_i z(2i) \times z^*(2i-2)$ and arg $\Sigma_i z(2i-1) \times z^*(2i+1)$ may be averaged to generate $vel_{subsampledAVG}$. The average is more generally expressed as:

$$vel_{subsampledAVG} \approx AVG(\{\delta v_d\} \mod 2\pi, \{\delta v_d'\} \mod 2\pi)$$

where term where $\delta$ is the subsample factor.

In act 40, a processor determines a degree of similarity between the color flow data estimated with the different PRF and flow sample counts. Two frames of data, such as frames of velocity, are compared to determine similarity.

For $vel_{times2} = \{2v_d\} \mod 2\pi$, then for areas that represent blood flow, $vel_{subsampled}$ and $vel_{times2}$ should have high spatial correlation. For artifacts that are random in nature, such as sparkle, their spatial correlation is low.

The similarity is determined as a function of location. The similarity between data from different frames is determined for each of the locations. The similarity may be difference. Alternatively, the similarity is based on kernels of any size (e.g., 5 axial and 3 lateral or the 2-D kernel size is 2A+1 samples axially×2B+1 samples laterally) centered at each location. The similarity is determined as a function of location.

Any measure of similarity may be used. In one embodiment, a minimum sum of absolute differences is used. In another embodiment, a correlation, such as a cross-correlation, is used. For example, the Doppler values from the sub-sampled estimation are correlated with the Doppler values from the full estimation multiplied by the sub-sampling factor. The cross-correlation or other similarity may be normalized. The degree of similarity may be quantified using normalized cross-correlation (NCC) between the two signals $vel_{subsampledAVG}$ and $vel_{times\delta}$. 2D Normalized cross-correlation using segments of data along the axial direction and lateral direction at zero lag is performed as follows:

$$\rho(i,j) = \frac{\sum_{l=j-B}^{j+B}\sum_{k=i-A}^{i+A} vel_{subsampledAVG}(k,l) vel_{times\delta}(k,l)}{\sqrt{\sum_{l=j-B}^{j+B}\sum_{k=i-A}^{i+A} vel_{subsampledAVG}(k,l)^2} \sqrt{\sum_{l=j-B}^{j+B}\sum_{k=i-A}^{i+A} vel_{times\delta}(k,l)^2}}$$

The normalized cross-correlation coefficient $\rho(i,j)$ at zero lag is calculated for every sample. Other correlation or similarity measures between the frames of data estimated with different PRF or flow sample count may be used.

In act 42, the processor detects the sparkle from the similarity. Locations with a high degree of correlation between data with different PRF are not sparkle, but are motion. Locations with a low degree of correlation are sparkle. The results of the correlation identify the locations with less correlation. Any threshold, such as an empirically developed threshold for a given imaging application, may be used to distinguish sparkle from motion.

In alternative embodiments, the processor does not specifically detect the sparkle or locations with sparkle. The similarity as a function of location may indicate the locations without specifically identifying a given location as sparkle. The detection is provided by creation of the similarity as a function of location.

In act 44, the processor or a filter filters a color flow image. The color flow image is velocity or other motion data to be used to generate an image (e.g., scalar estimate or Doppler values) or is RGB or other data for display. The color flow image is created from the estimates generated with the greater PRF, such as the velocities generated with the full sample count. Alternatively, the color flow image is created from the sub-sampling. In yet another alternative, the color flow image is created from samples from a different scan, so is not created from the data used for the determination of similarity.

The filtering is based on the degree of similarity as a function of location. To suppress the sparkle, the filtering more heavily reduces values at locations of less similarity. To enhance the sparkle, the filtering more heavily reduces values at locations of greater similarity. The filtering avoids altering some Doppler values, but reduces others. Alternatively, the filtering results in alteration of the magnitude of all of the values.

For velocity values, the reduction is moving the velocity closer to zero. The negative or positive velocities are reduced to lower negative or positive velocities while maintaining the sign. For energy values, the estimates are not signed. The reduction is moving the estimates closer to zero.

To reduce or filter, the motion data is multiplied by weights. The weights are fractional values between and/or including 0 and 1. Other weighting may be used, such as adding, subtracting, or dividing by weights. The color flow image or other motion data is weighted by the weights as a function of location.

The weights are mapped from the degree of similarity. A pixel-by-pixel or location specific weighting matrix is created. The degree of similarity for each location is mapped to a weight for that location. As a result, the weighting is target-dependent. The weights vary as a function of the level of similarity, providing for reduction as a function of sparkle, such as to pass motion signals and remove or attenuate sparkle artifact.

Any amount of reduction may be provided. For 2-D cross-correlation, normalized cross-correlation coefficients may range from −1 to 1 or from 0 to 1. Two signals are identical if the cross-correlation coefficient is 1 and they are considered uncorrelated if the coefficient is near or below zero. Any threshold within the range of normalized values may be used. In one embodiment, the threshold is used for binary weights. Above the threshold, the weight is 1 or 0. Below the threshold, the weight is the other of 0 or 1. Equal to the threshold may be mapped to either 0 or 1. The result is a binary mask as the filter. Values associated with sparkle are the only ones remaining or the only ones removed after filtering with the binary mask. The values associated with non-sparkle are removed or remain.

In one embodiment, if the normalized cross-correlation coefficient is greater than or equal to a set threshold value $\varepsilon>0$, then the sample value is multiplied by 0. If the coefficient is less than the threshold value $\varepsilon$, the sample value is multiplied by 1. This case may be used for enhancing kidney stones or gallstones where sparkle indicates desired information. The locations associated with greater similarity (i.e., with motion) are removed or reduced.

In another embodiment, if the coefficient is greater than or equal to a set threshold value $\varepsilon>0$, then the sample value will be multiplied by 1. If the coefficient is less than the threshold value $\varepsilon$, the sample value is multiplied by 0. The motion data for locations associated with lesser similarity (i.e., with sparkle) are removed or reduced, while motion data for motion locations is maintained.

Other weight mapping than a binary mask may be used. The weighting matrix may be generalized instead of using a mask of 0 and 1. Some examples of similarity to weight mapping are shown in FIGS. 2A-D. The normalized cross-correlation coefficient is mapped to weights. The maps of FIGS. 2A-D are for reducing velocity or other motion data at locations of sparkle. By applying the weights of FIGS. 2A-D, locations with greater similarity are weighted more strongly than locations with lesser similarity, reducing the Doppler values for the locations of the sparkle. Inverse maps may be used, weighting locations with lesser similarity more strongly than locations with greater similarity to reduce the Doppler values for the locations other than sparkle. Other linear or non-linear mapping of similarity to weights may be used.

In act 46, the filtered color flow image is displayed. The ultrasound system processes the filtered frame of data to create the image. Spatial filtering, temporal filtering, scan conversion, or other image processing is performed. The scalar values are mapped to display values, such as mapping to color values using a velocity scale. The resulting image is buffered for display. The display values are provided from the buffer to the display.

Color flow (e.g., Doppler energy or Doppler velocity), Doppler tissue motion, or other motion image is generated. The image may include other information. For example, the image is an overlay of the color flow data on B-mode data. For non-tissue locations or locations associated with sufficient flow, the color flow data (e.g., velocities) are used to determine a color to display. For tissue locations or low/no flow locations, the B-mode data is used.

The image includes motion values (e.g., velocities or energy) that have been altered to remove or reduce the sparkle artifact or motion information not associated with a rough surface. The color flow image, such as a velocity image, is generated from the Doppler values after the filtering based on similarity. As a result, the color flow image highlights stones or other rough surface targets without other motion information or highlights flow with less sparkle artifact. For example, a kidney stone or gallstone image is displayed. As another example, a velocity of fluid image is displayed.

Figure 3A:
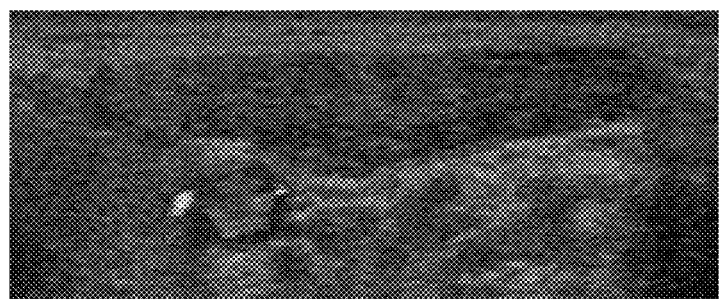
FIGS. 3A and 3B are example velocity images generated with different PRF.
Figure 3B:
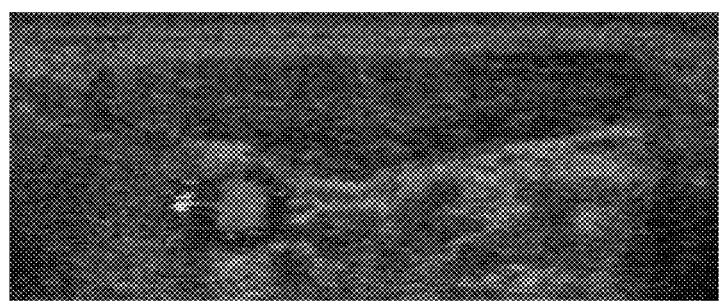
Figure 3C:
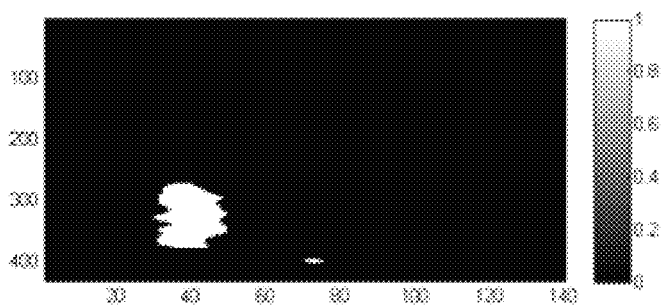
FIG. 3C is a binary filter or mask removing sparkle.
Figure 3D:
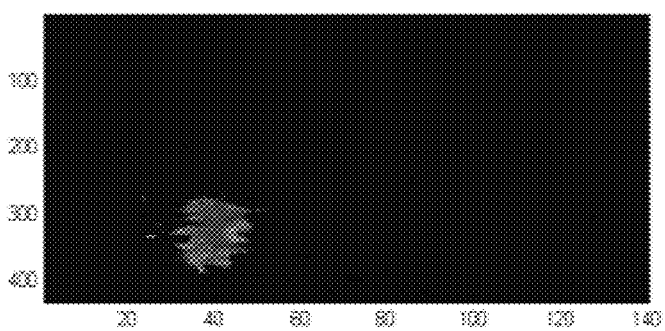
FIG. 3D is the flow image of FIG. 3A after applying the filter of FIG. 3C.
Figure 4A:
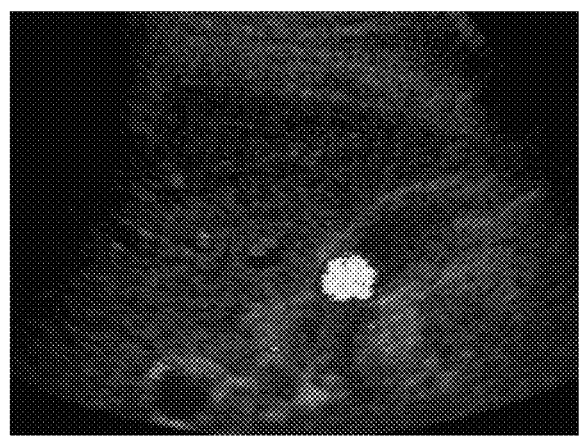
FIGS. 4A and 4B are example velocity images generated with different PRF.
Figure 4B:
Figure 4C:
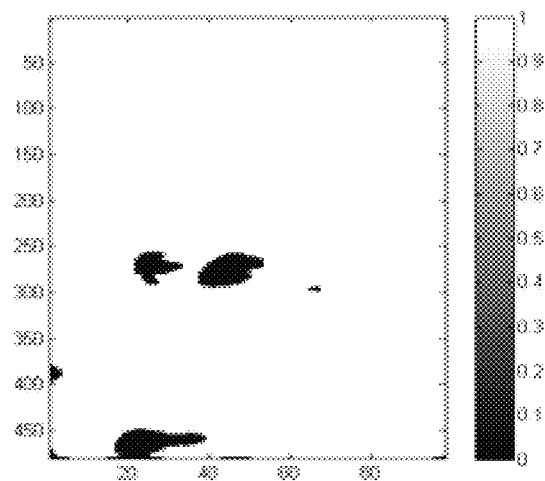
FIG. 4C is a binary filter or mask.

FIGS. 3A-D and 4A-C show two examples. FIGS. 3A-B and 4A-B show velocity images in combination with B-mode. The velocity information is color mapped. The velocity portions of these images represent frames of motion data. For FIGS. 3A and 4A, the images use estimates from a full flow sample count or higher PRF. For FIGS. 3B and 4B, the images use estimates from a sub-sampling of the same return samples by a factor of 2 (e.g., estimating velocity using every other sample of the full flow sample count). FIGS. 3B and 4B are from motion data estimated with a lower PRF.

FIG. 3C shows two white regions of no detected sparkle. Flow regions with correlation below a threshold are weighted by 0, resulting in the mask for passing clean flow of FIG. 3C. By applying the mask of FIG. 3C to the image of FIG. 3A, a velocity image of FIG. 3D results. The image has the sparkle removed or reduced. B-mode information may be provided for non-motion locations.

Figure 4D:
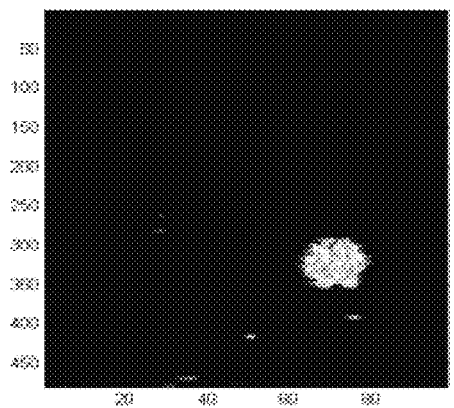
FIG. 4D is the flow image of FIG. 4A after filtering to enhance sparkle regions.

FIG. 4A shows a color flow image. A binary mask (e.g., FIG. 4C) passing (e.g., weight of 1) locations associated with sparkle and removing flow information not associated with sparkle is created by correlating the motion information of FIGS. 4A and 4B. By applying the resulting binary mask to FIG. 4A, the color flow or motion information for locations associated with sparkle is maintained while removing motion information for other locations. The resulting FIG. 4D shows color information as sparkle representing a kidney stone without flow from blood or tissue motion. B-mode information may be provided for non-motion locations.

FIG. 5 shows one embodiment of a system 10 for sparkle-based processing in flow images (i.e., in color flow, tissue motion, or other motion imaging). The system 10 implements the method of FIG. 1 or another method. By estimating motion data with different PRF, the motion data may be compared to indicate sparkle. The results of the comparison are used for processing, filtering, or other imaging based on detected sparkle locations.

The system 10 includes a transmit beamformer 12, a transducer 14, a receive beamformer 16, a memory 18, a filter 20, a flow estimator 22, another memory 28, a processor 24, and a display 27. Additional, different or fewer components may be provided. For example, the system includes a B-mode detector. As another example, the flow estimator 22 and processor 24 are provided without the front-end components, such as the transmit and receive beamformers 12, 16. In yet another example, the memories 18 and 28 are one component.

In one embodiment, the system 10 is a medical diagnostic ultrasound system. In an alternative embodiment, the system 10 is a computer or workstation. In yet another embodiment, the flow estimator 22 is part of a medical diagnostic ultrasound system or other medical imaging system, and the processor 24 is part of a separate workstation or remote system, making of the ultrasound imaging system.

The transducer 14 is an array of a plurality of elements. The elements are piezoelectric or capacitive membrane elements. The array is configured as a one-dimensional array, a two-dimensional array, a 1.5D array, a 1.25D array, a 1.75D array, an annular array, a multidimensional array, a wobbler array, combinations thereof, or any other now known or later developed array. The transducer elements transduce between acoustic and electric energies. The transducer 14 connects with the transmit beamformer 12 and the receive beamformer 16 through a transmit/receive switch, but separate connections may be used in other embodiments.

The transmit and receive beamformers 12, 16 are a beamformer for scanning a region of the patient with the transducer 14. The transmit beamformer 12, using the transducer 14, transmits one or more beams to scan a region. Vector®, sector, linear or other scan formats may be used. The receive lines and/or transmit beams are distributed in the scan region. The receive beamformer 16 samples the receive beams at different depths. Sampling the same locations at different times obtains a sequence for flow estimation.

The transmit beamformer 12 is a processor, delay, filter, waveform generator, memory, phase rotator, digital-to-analog converter, amplifier, combinations thereof or any other now known or later developed transmit beamformer components. In one embodiment, the transmit beamformer 12 digitally generates envelope samples. Using filtering, delays, phase rotation, digital-to-analog conversion, and amplification, the desired transmit waveform is generated. Other waveform generators may be used, such as switching pulsers or waveform memories.

The transmit beamformer 12 is configured as a plurality of channels for generating electrical signals of a transmit waveform for each element of a transmit aperture on the transducer 14. The waveforms are unipolar, bipolar, stepped, sinusoidal or other waveforms of a desired center frequency or frequency band with one, multiple, and/or fractional number of cycles. The waveforms have relative delay and/or phasing and amplitude for focusing the acoustic energy. The transmit beamformer 12 includes a controller for altering an aperture (e.g. the number of active elements), an apodization profile (e.g., type or center of mass) across the plurality of channels, a delay profile across the plurality of channels, a phase profile across the plurality of channels, center frequency, frequency band, waveform shape, number of cycles and/or combinations thereof. A transmit beam focus is generated based on these beamforming parameters.

The receive beamformer 16 is a preamplifier, filter, phase rotator, delay, summer, base band filter, processor, buffers, memory, combinations thereof or other now known or later developed receive beamformer components. The receive beamformer 16 is configured into a plurality of channels for receiving electrical signals representing echoes or acoustic energy impinging on the transducer 14. A channel from each of the elements of the receive aperture within the transducer 14 connects to an amplifier and/or delay. An analog-todigital converter digitizes the amplified echo signal. The digital radio frequency received data is demodulated to a base band frequency. Any receive delays, such as dynamic receive delays, and/or phase rotations are then applied by the amplifier and/or delay. A digital or analog summer combines data from different channels of the receive aperture to form return samples for one or a plurality of receive beams. The summer is a single summer or cascaded summer. In one embodiment, the beamform summer is configured to sum in-phase and quadrature channel data in a complex manner such that phase information is maintained for the formed beam. Alternatively, the beamform summer sums data amplitudes or intensities without maintaining the phase information.

The receive beamformer 16 is configured to form receive beams in response to the transmit beams. For example, the receive beamformer 16 receives one, two, or more receive beams in response to each transmit beam. The receive beams are collinear, parallel and offset or nonparallel with the corresponding transmit beams. The receive beamformer 16 outputs spatial samples representing different spatial locations of a scanned region. Once the channel data is beamformed or otherwise combined to represent spatial locations along the scan lines 11, the data is converted from the channel domain to the image data domain. The phase rotators, delays, and/or summers may be repeated for parallel receive beamformation. One or more of the parallel receive beamformers may share parts of channels, such as sharing initial amplification.

For imaging motion, such as tissue motion or fluid velocity, multiple transmissions and corresponding receptions are performed for each of a plurality of substantially same spatial locations. Phase changes between the different receive events for each given location indicate the velocity of the tissue or fluid. A velocity sample group corresponds to multiple transmissions for each of a plurality of scan lines 11. The number of times a substantially same spatial location, such as a scan line 11, is scanned within a velocity sample group is the velocity or flow sample count. The transmissions for different scan lines 11, different velocity sample groupings or different types of imaging may be interleaved. The amount of time between transmissions to a substantially same scan line 11 within the velocity sample count is the pulse repetition interval. The pulse repetition interval establishes the pulse repetition frequency or vice versa.

The memory 18 is video random access memory, random access memory, removable media (e.g. diskette or compact disc), hard drive, database, corner turning memory, or other memory device for storing data or video information. In one embodiment, the memory 18 is a corner turning memory of a motion parameter estimation path. The memory 18 is configured to store signals responsive to multiple transmissions along a substantially same scan line. The memory 22 is configured to store ultrasound data formatted in an acoustic grid, a Cartesian grid, both a Cartesian coordinate grid and an acoustic grid, or ultrasound data representing a volume in a 3D grid. The return samples of the flow sample count for each of a plurality of locations are stored.

The filter 20 is a clutter filter, finite impulse response filter, infinite impulse response filter, analog filter, digital filter, combinations thereof or other now known or later developed filter. In one embodiment, the filter 20 includes a mixer to shift signals to baseband and a programmable low pass filter response for removing or minimizing information at frequencies away from the baseband. In other embodiments, the filter 20 is a low pass, high pass, or band pass filter. The filter 20 reduces velocities from fluids or alternatively reduces the influence of data from tissue while maintaining velocity information from fluids. The filter 20 has a set response or may be programmed, such as altering operation as a function of signal feedback or other adaptive process. In yet another embodiment, the memory 18 and/or the filter 20 are part of the flow estimator 22.

The Doppler or flow estimator 22 is a Doppler processor or cross-correlation processor for estimating the color flow data. In alternative embodiments, another device now known or later developed for estimating velocity, power (e.g., energy), and/or variance from any or various input data may be provided. The flow estimator 22 receives a plurality of signals associated with a substantially same location at different times and estimates a Doppler shift frequency, based on a change or an average change in phase between consecutive signals from the same location. Velocity is calculated from the Doppler shift frequency. Alternatively, the Doppler shift frequency is used as a velocity. The power and variance may also be calculated.

Color flow data (e.g., velocity, power, and/or variance) is estimated for spatial locations in the scan region from the beamformed scan samples. For example, the flow data represents a plurality of different locations in a plane. The color flow data is motion data for tissue and/or fluid.

The flow estimator 22 may apply one or more thresholds to identify sufficient motion information. For example, velocity and/or power thresholding for identifying velocities is used. In alternative embodiments, a separate processor or filter applies thresholds. In other embodiments, the thresholding is applied after any motions suppression, such as by the processor 24.

The flow estimator 22 outputs frames of data representing the scan region at different times. The beamformed samples for a given flow sample count are used to estimate for a time. A moving window with overlap of the data is used to estimate for other times. Velocities for each location at different times are output.

Two or more frames are estimated from the scanning for the same locations. The frames are for a same or different time. For sequential scanning, the frames represent the locations at different times. Where the samples for the same flow sample count are used to estimate the frames, then the frames represent a same time.

The two or more frames are estimated differently. The number of samples used in the estimation for each frame is different. The PRF or flow sample count in the estimation varies from frame-to-frame. For example, 16 samples are obtained and used for estimating velocity in one frame. Every other sample (e.g., 8 samples) is used to estimate the velocity in the other frame. The sub-sampling factor for the other frame is 2. A different number of samples are used to estimate the velocities of the two frames.

The flow estimator 22 or the processor 24 is configured to normalize the motion data of the two or more frames. Due to sub-sampling, the velocities estimation may be different, such as the sub-sampling by the factor of 2 leading to the results of the autocorrelation being doubled relative to the frame estimated from the full flow sample count. The motion data from the full flow sample count is multiplied to normalize. Alternatively, multiplication or normalization is not performed, and the frames are used despite having different magnitude ranges.

The processor 24 is a digital signal processor, a general processor, an application specific integrated circuit, field programmable gate array, control processor, digital circuitry, analog circuitry, graphics processing unit, filter, combinations thereof or other now known or later developed device for implementing calculations, algorithms, programming or other functions. The processor 24 operates pursuant to instruction provided in the memory 28, or a different memory for sparkle-based image processing. Additional or multiple processors may be used. The processor 24 is configured by software, firmware, and/or hardware.

The processor 24 receives color flow data from the flow estimator 22, the memory 28, and/or another source. Using the received motion data, the processor 24 is configured to identify which of the locations of the scan region correspond to sparkle in the estimates. The processor 24 is configured to compare the motion values from the different frames. For example, a spatial cross-correlation between the data of the frames is performed. The cross-correlation indicates a level of similarity between the different PRF frames. Similarity is determined for each of multiple locations represented in the frames. The locations with less correlation between motion values estimated from different PRF are locations of sparkle. The locations with more correlation are actual motion rather than sparkle.

The processor 24 specifically identifies locations of sparkle. Alternatively or additionally, the processor 24 uses the indication of sparkle provided by the level of similarity for filtering or other image processing. The level of similarity may be mapped to filter weights. The weights are applied to a frame of motion values, such as to the frame estimated using the greater number of samples. The mapping and corresponding weights reduce locations not associated with sparkle or locations associated with sparkle. Other locations are maintained the same, increased, or not reduced as mush. The weight matrix and/or locations of sparkle may be filtered, such as with a low pass filter, to remove outlier locations or reduce outlier weights.

The processor 24 or other component uses the filtered motion values to generate an image. The frame is scan converted and color mapped. The resulting color values are added to a B-mode image, such as an overlay, or used alone. The color values are placed in a display buffer to display an image on the display 27.

The display 27 is a CRT, LCD, plasma, projector, monitor, printer, touch screen, or other now known or later developed display device. The display 27 receives RGB, other color values, or other motion values and outputs an image. The image may be a gray scale or color image. The image represents the region of the patient scanned by the beamformer and transducer 14, but with returns from sparkle locations removed, reduced, or maintained while reducing returns for other locations. The display 27 displays a Doppler or other color image from the motion values as filtered. The resulting image may represent rough surfaces, such as from stones, without or with less information from fluid flow or tissue motion. Alternatively, the resulting image may represent fluid flow or tissue motion without or with less information from sparkle artifact.

The memory 28 is video random access memory, random access memory, removable media (e.g. diskette or compact disc), hard drive, database, or other memory device for storing color flow or other motion data. The stored data is in a polar or Cartesian coordinate format. The memory 28 is used by the processor 24 for the various filtering, detecting, identifying, correlation, calculating, or other acts.

The instructions for implementing the processes, methods and/or techniques discussed above are provided on computer-readable storage media or memories, such as a cache, buffer, RAM, removable media, hard drive or other computer readable storage media. The memory 28 or other memory stores the instructions for sparkle detection in Doppler imaging. Non-transitory computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for sparkle artifact detection in color flow, the method comprising:
    generating first color flow data representing locations in a patient, the first color flow data generated with a first pulse repetition frequency;
    generating second color flow data representing the locations in the patient, the second color flow data generated with a second pulse repetition frequency, the second pulse repetition frequency different than the first pulse repetition frequency;
    determining a degree of similarity between the first and second color flow data for each of the locations;
    distinguishing sparkle from motion based on the degree of similarity for each of the locations;
    filtering a color flow image, the filtering suppressing or enhancing locations of the sparkle based on the degree of similarity as a function of the location; and
    displaying the filtered color flow image.

2. The method of claim 1 wherein generating the first and second color flow data comprises transmitting sequentially at the first and second different pulse repetition frequencies, respectively.

3. The method of claim 1 wherein determining comprises performing normalized cross-correlation between the first and second color flow data.

4. The method of claim 1 wherein filtering comprises mapping weights as a function of the degree of similarity by location and weighting the color flow image as a function of the locations with the weights.

5. The method of claim 1 wherein filtering comprises weighting locations with lesser similarity more strongly than locations with greater similarity, and wherein displaying comprises displaying a kidney or gallstone image.

6. The method of claim 1 wherein filtering comprises weighting locations with greater similarity more strongly than locations with lesser similarity, and wherein displaying comprises displaying a velocity of fluid image.

7. The method of claim 1 wherein filtering comprises applying binary weights as a function of the degree of similarity.

8. The method of claim 1 wherein generating the first color flow data comprises transmitting with the first pulse repetition frequency and wherein generating the second color flow data comprises sub-sampling returns from the transmitting.

9. The method of claim 8 wherein generating the first color flow further comprises estimating velocity from the returns and multiplying the estimated velocities by two, and wherein sub-sampling comprises sub-sampling by a factor of two.

\* \* \* \* \*